(12) United States Patent
Finn et al.

(10) Patent No.: US 8,748,170 B2
(45) Date of Patent: Jun. 10, 2014

(54) POLYPEPTIDES DERIVED FROM CYCLIN B1 AND USES THEREOF

(75) Inventors: Olivera J. Finn, Pittsburgh, PA (US); Laura A. Vella-Geynisman, Chicago, IL (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 427 days.

(21) Appl. No.: 13/055,907

(22) PCT Filed: Jul. 27, 2009

(86) PCT No.: PCT/US2009/051853
§ 371 (c)(1),
(2), (4) Date: Aug. 8, 2011

(87) PCT Pub. No.: WO2010/011994
PCT Pub. Date: Jan. 28, 2010

(65) Prior Publication Data
US 2011/0280897 A1 Nov. 17, 2011

Related U.S. Application Data

(60) Provisional application No. 61/083,800, filed on Jul. 25, 2008.

(51) Int. Cl.
*C07K 14/435* (2006.01)
*C07K 7/08* (2006.01)
*C07H 21/04* (2006.01)
*C12N 7/00* (2006.01)
*C12N 7/01* (2006.01)

(52) U.S. Cl.
USPC ........ 435/320.1; 530/300; 530/324; 530/326; 530/327; 536/23.5

(58) Field of Classification Search
None
See application file for complete search history.

(56) References Cited

U.S. PATENT DOCUMENTS

| | | | |
|---|---|---|---|
| 5,424,398 A | 6/1995 | Middeldorp et al. | |
| 5,543,291 A | 8/1996 | Keyomarsi et al. | |
| 5,788,963 A | 8/1998 | Murphy et al. | |
| 5,846,827 A | 12/1998 | Celis et al. | |
| 5,962,318 A | 10/1999 | Rooney et al. | |
| 5,973,119 A | 10/1999 | Coats et al. | |
| 6,225,443 B1 | 5/2001 | DeMars et al. | |
| 6,660,511 B1 * | 12/2003 | Luo et al. | 435/196 |
| 6,805,861 B2 | 10/2004 | Stauss | |
| 7,704,507 B2 | 4/2010 | Finn et al. | |
| 2002/0055627 A1 | 5/2002 | Rosen et al. | |
| 2002/0090362 A1 | 7/2002 | Stauss | |
| 2002/0150891 A1 | 10/2002 | Hood et al. | |
| 2003/0040617 A9 | 2/2003 | Rosen et al. | |
| 2003/0143647 A1 | 7/2003 | Finn et al. | |
| 2006/0147460 A1 | 7/2006 | Finn et al. | |

FOREIGN PATENT DOCUMENTS

| | | |
|---|---|---|
| WO | 96/12406 A1 | 5/1996 |
| WO | 98/33450 A1 | 8/1998 |
| WO | 99/60119 A2 | 11/1999 |
| WO | 00/55351 A1 | 9/2000 |
| WO | 03/033520 A2 | 4/2003 |
| WO | 2005/113595 A2 | 12/2005 |
| WO | 2007/044033 A2 | 4/2007 |
| WO | WO-2009129498 A2 * | 10/2009 |
| WO | 2010/011994 A2 | 1/2010 |

OTHER PUBLICATIONS

Egloff et al. Cyclin B1 and other cyclins as tumor antigens in immunosurveillance and immunotherapy of cancer. Cancer Res 66: 6-9, 2006.*
Kwissa et al. The science of adjuvants. Expert Rev Vaccines 6(5): 673-684, 2007.*
UniProtKB/Swiss-Prot Accession No. P14635.1, Apr. 1, 1990; 8 pages.*
Pines et al. Isolation of a human cyclin cDNA: evidence for ccylin mRNA and protein regulation in the cell cycle and for interaction with p34cdc2. Cell 58(5): 833-846, 1989.*
Vella et al. Immunity against cyclin B1 tumor antigen delays development of spontaneous cyclin B1-positive tumors in p53-/-mice. Ann NY Acad Sci 1174: 68-73, 2009.*
Wang et al. Lyophilization and development of solid protein pharmaceuticals. Int J Pharmaceutics 203: 1-60, 2000.*
Song et al. Cancer stem cells—an old idea that's new again: implications for the diagnosis and treatment of breast cancer. Expert Opin Biol Ther 7(4): 431-438, 2007.*
Tannock and Hill. The Basic Science of Oncology. 1998. New York: McGraw-Hill;; p. 357.*
GenBank Accession No. 2JGZ_B, "Chain B, Crystal Structure of Phospho-Cdk2 In Complex With Cyclin B." (Jun. 20, 2007) Retrieved on Feb. 27, 2010.
GenBank Accession No. AAV38930.1 "Cyclin B1 [*Homo sapiens*]." (Oct. 28, 2004) Retrieved on Feb. 27, 2010.

(Continued)

*Primary Examiner* — Bridget E Bunner
(74) *Attorney, Agent, or Firm* — Leydig, Voit & Mayer, Ltd.

(57) ABSTRACT

In one embodiment, the invention provides a composition comprising one or more polypeptide(s), each of said polypeptide(s) comprising a sequence selected from the group consisting of KFRLLQETMYMTVSI (SEQ ID NO: 1), LQETMYMTVSIIDRF (SEQ ID NO: 2), and MYMTVSIIDRFM (SEQ ID NO: 3), or a combination of two or three such polypeptides, wherein each of said polypeptide(s) consist(s) of at most 24 amino acid residues, the composition also comprising a carrier. In another embodiment, the invention provides a composition comprising one or more bacterial or viral vectors comprising one or more nucleic acid molecule(s) encoding one or more polypeptide(s), each of said polypeptide(s) having a sequence selected from the group consisting of KFRLLQETMYMTVSI (SEQ ID NO: 1), LQETMYMTVSIIDRF (SEQ ID NO: 2), and MYMTVSIIDRFM (SEQ ID NO: 3), wherein each of said polypeptide(s) consist(s) of at most 24 amino acid residues.

26 Claims, 4 Drawing Sheets

(56) References Cited

OTHER PUBLICATIONS

Figure 1B:
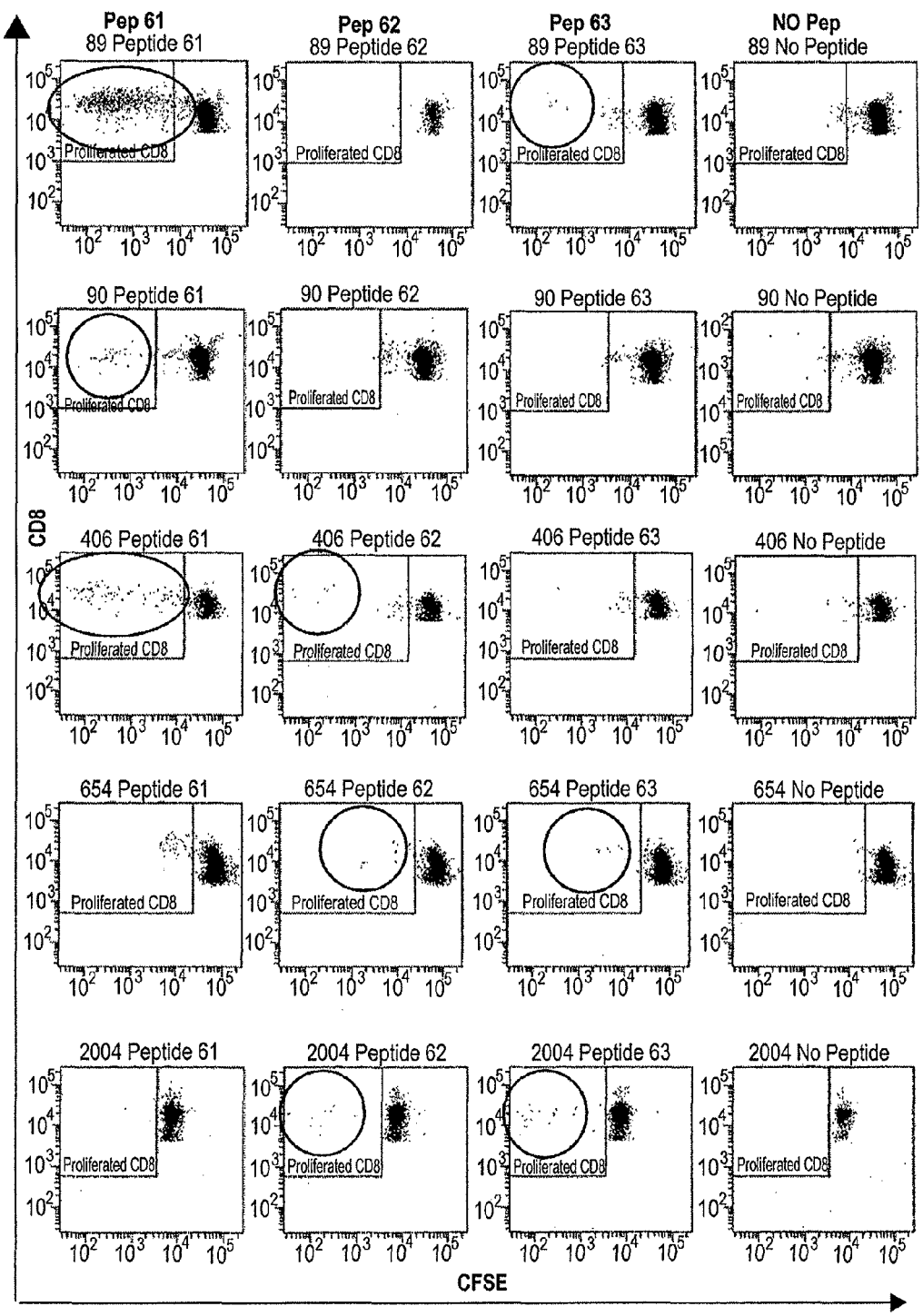
Figure 2A:
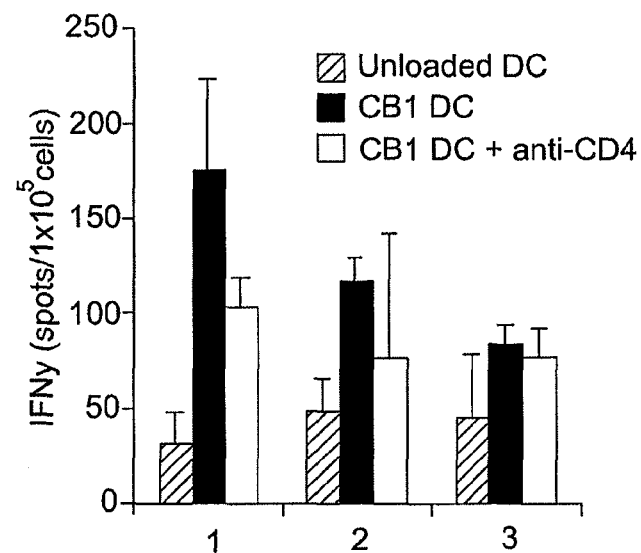
Figure 2B:
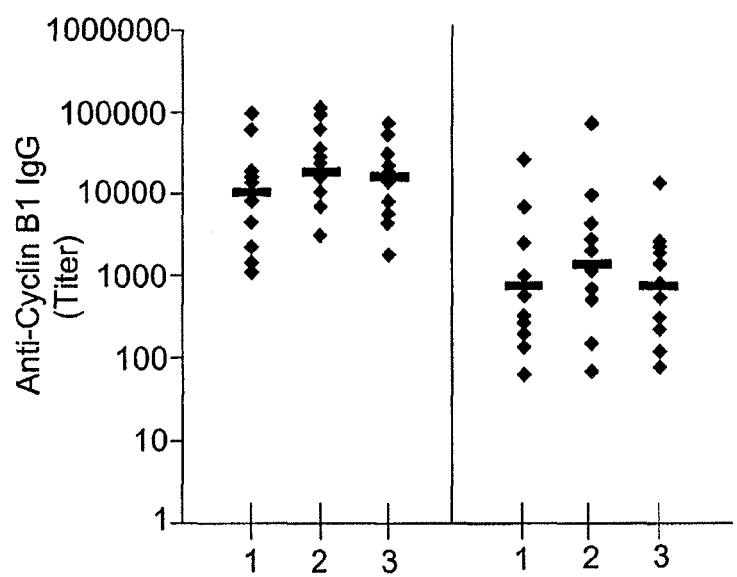
Figure 2C:
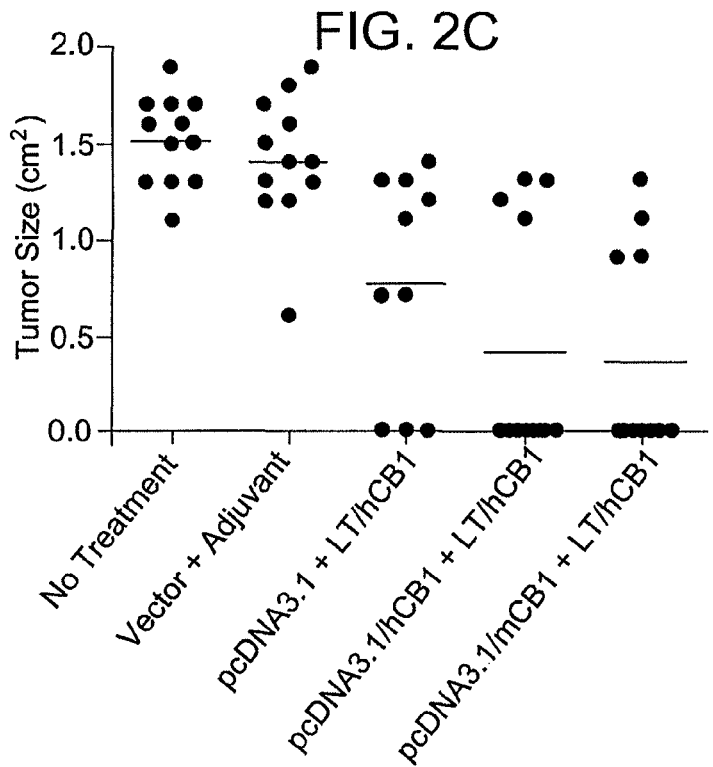
Figure 2D:
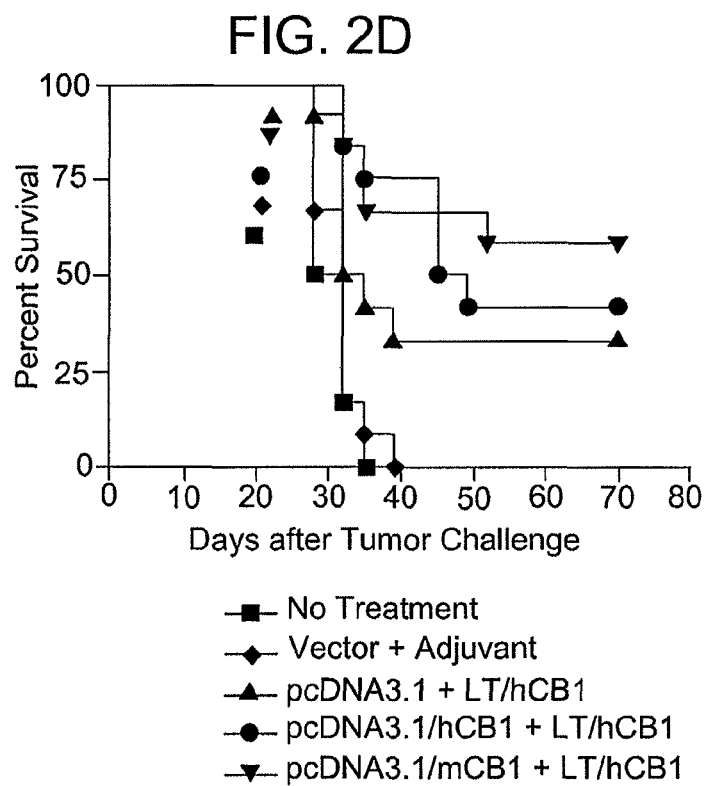

GenBank Accession No. BAF82120.1 "Unnamed protein product [*Homo sapiens*]." (Jan. 9, 2008) Retrieved on Feb. 27, 2010.
Maecker et al., "Use of overlapping peptide mixtures as antigens for cytokine flow cytometry," *Journal of Immunological Methods*, 255: 27-40 (2001).
Petri et al., "The Crystal Structure of Human Cyclin B," *Cell Cycle*, 6(11): 1342-1349 (Jun. 1, 2007).
Vella, et al., "Healthy individuals have T-cell and antibody responses to the tumor antigen cyclin B1 that when elicited in mice protect from cancer," *PNAS*, 106(33): 14010-14015 (Aug. 18, 2009).
U.S. Appl. No. 60/324,450, filed Sep. 24, 2001, Finn et al.
U.S. Appl. No. 60/634,072, filed Dec. 7, 2004, Finn et al.
U.S. Appl. No. 61/083,800, filed Jul. 25, 2008, Finn et al.
Aarnoudse et al., "TCR Reconstitution in Jurkat Reporter Cells Facilitates the Identification of Novel Tumor Antigens by CDNA Expression Cloning," *Int. J Cancer*, 99(1): 7-13 (May 1, 2002).
Adams et al., "High Affinity Restricts the Localization and Tumor Penetration of Single-Chain Fv Antibody Molecules," *Cancer Res*, 61(12): 4750-4755 (Jun. 15, 2001).
Alajez, "MHC-Unrestricted MUC1-Specific T Cell Receptor for Cancer Immunotherapy/Gene Therapy," University of Pittsburgh, Thesis Dissertation submitted Dec. 8, 2003 1-123.
Alajez et al., "Therapeutic potential of a tumor-specific, MHC-unrestricted T-cell receptor expressed on effector cells of the innate and the adaptive immune system through bone marrow transduction and immune reconstitution," *Blood*, 105(12): 4583-4589 (Jun. 15, 2005).
Altschul et al., "Basic Local Alignment Search Tool," *J Mol Biol*, 215(3): 403-410 (1990).
Attword, "The Babel of Bioinformatics," *Science*, 290: 471-473 (Oct. 20, 2000).
Avigan et al., "Immune Reconstitution Following High-Dose Chemotherapy With Stem Cell Rescue in Patients With Advanced Breast Cancer," *Bone Marrow Transplant*, 26(2): 169-176 (Jul. 2, 2000).
Badou et al., "Mercuric Chloride-Induced Autoimmunity," *Current Protocols in Immunology*, 3(Supplement 32): 15.15.1-15.15.18 (Aug. 1999).
Barany et al., "Solid-phase peptide synthesis: a silver anniversary report," *Int. J. Peptide Protein Res. 30*: 705-739 (1987).
Barnd et al., "Specific, Major Histocompatibility Complex-Unrestricted Recognition of Tumor-Associated Mucins by Human Cytotoxic T Cells," *Proc Natl Acad Sci U S A,*, 86: 7159-7163 (Sep. 1989).
Barratt-Boyes, "Making the Most of Mucin: A Novel Target for Tumor Immunotherapy," *Cancer Immunology Immunotherapy*, 43(3): 142-151 (1996).
Bensinger et al., "High-Dose Busulfan, Melphalan, Thiotepa and Peripheral Bolld Stem Cell Infusion for the Treatment of Metastatic Breast Cancer," *Bone Marrow Transplant*, 19(12): 1183-1189 (Jun. 2, 1997).
Berard et al., "Cross-Priming of Naïve CD8 T Cells Against Melanoma Antigens Using Dendritic Cells Loaded With Killed Allogeneic Melanoma Cells," *J. Exp. Med.*, 192(11): 1535-1543 (Dec. 4, 2000).
Berkner, "Development of Adenovirus Vectors for the Expression of Heterologous Genes," *Bio Techniques*, 6(7): 616-629 (Jul./Aug. 1988).
Blake et al., "Use of Combinatorial Peptide Libraries to Construct Functional Mimics of Tumor Epitopes Recognized by MHC Class I-Restricted Cytolytic T Lymphocytes," *The Journal of Experimental Medicine*, 184(1): 121-130 (Jul. 1, 1996).
Boel et al., "BAGE: a New Gene Encoding an Antigen Recognized on Human Melanomas by Cytolytic T Lymphocytes," *Immunity*, 2: 167-175 (Feb. 1995).
Bozzacco et al., "DEC-205 receptor on dendritic cells mediates presentation of HIV gag protein to CD8+ T cells in a spectrum of human MHC I haplotypes," *Proc. Nat. Acad. Sci. USA*, 104(4): 1289-1294 (Jan. 23, 2007).
Brenner et al., "Gene Marking to Determine Whether Autologous Marrow Infusion Restores Long-Term Haemopoiesis in Cancer Patients," *Lancet*, 342(8880): 1134-1137 (Nov. 6, 1993).
Brichard et al., "The Tyrosinase Gene Codes for an Antigen Recognized by Autologous Cytolytic T Lymphocytes on HLA-A2 Melanomas," *The Journal of Experimental Medicine*, 178(2): 489-495 (Aug. 1, 1993).
Bubenik, "Tumour MHC Class I Downregulation and Immunotherapy," *Oncol Rep*, 10(6): 2005-2008 (Dec. 2003).
Burchell et al., "A Short Sequence, Within the Amino Acid Tandem Repeat of a Cancer-Associated Mucin, Contains Immunodominant Epitopes," *Int J Cancer*, 44(4): 691-696 (Oct. 15, 1989).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *The Journal of Cell Biology*, 111: 2129-2138 (Nov. 1990).
Byun et al., "Analysis of the relative level of gene expression from different retroviral vectors used for gene therapy," *Gene Ther.* 3(9): 780-789 (Sep. 1996).
Callan et al., "Selection of T Cell Receptor Variable Gene-Encoded Amino Acids on the Third Binding Site Loop: A Factor Influencing Variable Chain Selection In a T Cell Response," *Eur J Immunol*, 25(6): 1529-1534 (Jun. 1995).
Chen et al., "A testicular antigen aberrantly expressed in human cancers detected by autologous antibody screening," *Proc. Natl. Acad. Sci. USA*, 94(5): 1914-1918 (Mar. 4, 1997).
Chung et al., "Functional Three-Domain Single-Chain T-Cell Receptors," *Proc Nati Acad Sci U S A*, 91: 12654-12658 (Dec. 1994).
Clauser et al., "Role of Accurate Mass Measurement (±10 ppm) in Protein Identification Strategies Employing MS or MS/MS and Database Searching," *Analytical Chemistry*, 71(14): 2871-2882 (Jul. 15, 1999).
Coulie et al., "A New Gene Coding for a Differentiation Antigen Recognized by Autologous Cytolytic T Lymphocytes on HLA-A2 Melanomas," *The Journal of Experimental Medicine*, 180(1): 35-42 (Jul. 1, 1994).
Covini et al., "Immune Response to Cyclin B1 in Hepatocellular Carcinoma," *Hepatology*, (PubMed Abstract ID 8985268), 25(1): 75-80 (Jan. 1997).
Crystal et al., "A Phase 1 Study, In Cystic Fibrosis Patients, of the Safety, Toxicity, and Biological Efficacy of a Single Administration of a Replication Deficient, Recombinant Adenovirus Carrying the cDNA of the Normal Cystic Fibrosis Transmembrane Conductance Regulator Gene in the Lung," *Human Gene Ther.*, 6(5): 643-666 (May 1995).
Crystal et al., "Evaluation of Repeat Administration of a Replication Deficient, Recombinant Adenovirus Containing the Normal Cystic Fibrosis Transmembrane Conductance Regulator cDNA to the Airways of Individulas with Cystic Fibrosis," *Human Gene Ther.*, 6(5): 667-703 (May 1995).
Davis et al., "Anti-Idiotype Antibodies Can Induce Long-Term Complete Remissions in Non-Hodgkin's Lymphoma Without Eradicating the Malignant Clone," *Blood*, 92(4): 1184-1190 (Aug. 15, 1998).
De Boer et al., "Cyclin D1 Protein Analysis in the Diagnosis of Mantle Cell Lymphoma," *Blood*, 86(7): 2715-2723 (Oct. 1, 1995).
Derby et al., "Two Internediate-Avidity Cytotoxic T Lymphocyte Clones With a Disparity Between Functional Avidity and MHC Tetramer Staining," *Int Immunol*, 13(6): 817-824 (Jun. 2001).
Diefenbach et al., Rae1 and H60 Ligands of the NKG2D Receptor Stimulate Tumour Immunity, *Nature*, 413(6852): 165-171 (Sep. 13, 2001).
Disi et al., "HER-2/neu Oncogenic Protein: Issues in Vaccine Development," *Critical Reviews in Immunology*, 18(1&2): 37-45 (1998).
Dong et al., "Prognostic Significance of Cyclin E Overexpression in Laryngela Squamous Cell Carcinomas," *Clinical Cancer Research*, 6(11): 4253-4258 (Nov. 2000).
Dudley et al., "A Phase I Study of Nonmyeloablative Chemotherapy and Adoptive Transfer of Autologous Tumor Antigen-Specific T Lymphocytes in Patients With Metastatic Melanoma," *J. Immunother*, 25(3): 243-251 (May/Jun. 2002).
Dudley et al., "Cancer Regression and Autoimmunity in Patients After Clonal Repopulation with Antitumor Lymphocytes," *Science*, 298(5594): 850-854 (Oct. 25, 2002).

(56) References Cited

OTHER PUBLICATIONS

Dutta et al., "Cyclins as Markers of Tumor Proliferation: Immunocytochemical Studies in Breast Cancer," *Proc. Natl. Acad. Sci. USA*, 92(12): 5386-5390 (Jun. 6, 1995).
Eng et al., "An Approach to Correlate Tandem Mass Spectral Data of Peptides with Amino Acid Sequences in a Protein Database," *Journal of the American Society for Mass Spectrometry*, 5(11): 976-989 (Nov. 1994).
Engel et al., "High-Efficiency Expression and Solubilization of Functional T Cell Antigen Receptor Heterodimers," *Science*, 256(5061): 1318-1321 (May 29, 1992).
Eshhar et al., "The T-Body Approach: Potential for Cancer Immunotherapy," *Springer Semin Immunopathol*, 18(2): 199-209 (1996).
Fay et al., "Long-term outcomes in patients with metastatic melanoma vaccinated with melanoma peptide-pulsed $CD34^+$ progenitor-derived dendritic cells," *Cancer Immunol. Immunother*, 55: 1209-1218 (2006).
Fernandez et al., "Dendritic Cells Directly Trigger NK Cell Functions: Cross-talk Relevant in Innate Anti-Tumor Immune Responses In Vivo," *Nat Med*, 5(4): 405-411 (Apr. 1999).
Finn et al., "MUC-1 Epithelial Tumor Mucin-Based Immunity and Cancer Vaccines," *Immunological Reviews*, 145: 61-89 (1995).
Fisk et al., "Identification of an Immunodominant Peptide of HER-2/neu Protooncogene Recognized by Ovarian Tumor-specific Cytotoxic T Lymphocyte Lines," *The Journal of Experimental Medicine*, 181(6): 2109-2117 (Jun. 1995).
Fontenot et al., "Biophysical Characterization of One-, Two-, and Three-Tandem Repeats of Human Mucin (muc-1) Protein Core," *Cancer Research*, 53(22): 5386-5394 (Nov. 15, 1993).
Fontenot et al., "Structure of a Tumor Associated Antigen Containing a Tandemly Repeated Immunodominant Epitope," *Journal of Biomolecular Structure & Dynamics*, 13(2): 245-260 (Oct. 1995).
Freshney, Culture of Animal Cells, A Manual of Basic Technique, (Alan R. Liss, Inc., New York, NY 1983) 4.
Garcia et al., "An $\alpha\beta$ Cell Receptor Structure at 2.5 A and Its Orientation in the TCR-MHC Complex," *Science*, 274(5285): 209-219 (Oct. 11, 1996).
Gaugler et al., "Human Gene MAGE-3 Codes for an Antigen Recognized on a Melanoma by Autologous Cytolytic T Lymphocytes," *The Journal of Experimental Medicine*, 179: 921-930 (Mar. 1994).
Gregoire et al., "Covalent Assembly of a Soluble T Cell Receptor-Peptide-major Histocompatibility Class I Complex," *Natl Acad Sci U S A*, 93(14): 7184-7189 (Jul. 1996).
Groner et al., "Cytotoxic T-cells with grafted, tumor-specific recognition functions," *European Journal of Cancer*, 32: S20 (Jun. 1997).
Gura, "Systems for Identifying New Drugs Are Often Faulty," *Science*, 278: 1041-1042 (1997).
Hanenberg et al., "Colocalization of Retrovirus and Target Cells on Specific Fibronectin Fragments Increases Genetic Transduction of Mammalian Cells," *Nature Medicine*, 2(8): 876-882 (Aug. 1996).
Hassan et al., "Clinical Significance of Cyclin B1 Protein Expression in Squamous Cell Carcinoma of the Tongue," *Clinical Cancer Research*, 7: 2458-2462 (Aug. 2001).
Henderson et al., "Human Tumor Antigens Are Ready to Fly," *Advances in Immunology*, 62: 217-256 (1996).
Herman et al., "A Peptide Encoded by the Human MAGE3 Gene and Presented by HLA-B44 Induces Cytolytic T Lymphocytes That Recognize Tumor Cells Expressing MAGE3," *Immunogenetics*, 43(6): 377-383 (1996).
Herr et al., "Detection and quantification of blood-derived $CD8^+$ T lymphocytes secreting tumor necrosis factor $\alpha$ in response to HLA-A2.1-binding melanoma and viral peptide antigens," *Journal of Immunological Methods*, 191(2): 131-142 (1996).
Hiltbold et al., "Presentation of MUC1 Tumor Antigen by Class I MHC and CTL Function Correlate with the Glycosylation State of the Protein Taken Up by Dendritic Cells," *Cellular Immunology*, 194(2): 143-149 (Jun. 15, 1999).
Holmberg et al., "High-Dose Busulfan, Melphalan and Thiotepa Followed by Autologous Peripheral Blood Stem Cell (PBSC) Rescue in Patients With Advanced Stage III/IV Ovarian Cancer," *Bone Marrow Transplant*, 22(7): 651-659 (Oct. 1, 1998).
Holmberg et al., "Clinical Outcome of Breast and Ovarian Cancer Patients Treated With High-Dose Chemotherapy, Autologous Stem Cell Rescue and Theratope STn-KLH Cancer Vaccine," *Bone Marrow Transplant*, 25(12): 1233-1241 (Jun. 2, 2000).
Hunt et al., "Characterization of Peptides Bound to the Class I MHC Molecule HLA-A2.1 by Mass Spectrometry," *Science*, 255(5049): 1261-1263 (Mar. 6, 1992).
Hunt et al., "Peptides Presented to the Immune System by the Murine Class II Major Histocompatibility Complex Molecule I-$A^d$," *Science*, 256(5065): 1817-1820 (Jun. 26, 1992).
Ikeda et al., "Characterization of an Antigen That Is Recognized on a Melanoma Showing Partial HLA Loss by CTL Expressing an NK Inhibitory Receptor," *Immunity*, 6: 199-208 (Feb. 1997).
Jaffe et al., "Adenoviral Mediated Transfer and Expression of a Normal Human $\alpha1$-Antitrypsin cDNA in Primary Rat Hepatocytes," *Clinical Research*, 39(2): 302A (1991).
Jemal et al., "Cancer Statistics, 2003," *CA Cancer J Clin*, 53(1): 5-26 (Jan./Feb. 2003).
Jerome et al., "Cytotoxic T-Lymphocytes Derived from Patients with Breast Adenocarcinoma Recognize an Epitope Present on the Protein Core of a Mucin Molecule Preferentially Expressed by Malignant Cells," *Cancer Research*, 51(11): 2908-2916 (Jun. 1, 1991).
Jones et al., "Improved Methods for Building Protein Models in Electron Density Maps and the Locations of Errors in These Models." *Acta Crystallographica*, A47, (Pt 2): 110-119 (Mar. 1, 1991).
Kao et al., "A New Strategy for Tumor Antigen Discovery Based on in Vitro Priming of Naïve T Cells with Dendritic Cells," *Clinical Cancer Research*, 7(3 Supplement): 773s-780s (Mar. 2001).
Kao et al., "Identification of Cyclin B1 as an Epithelial Tumor Antigen," *FASEB Journal*, (Abstract 949.6) 15(5): A1206 (Mar. 8, 2001).
Kao et al., "Identification of Cyclin B1 as a Shared Human Epithelial Tumor-Associated Antigen Recognized by T Cells," *J. Exp. Med.* 194(9): 1313-1323 (Nov. 5, 2001).
Kawakami et al., "Identification of a human melanoma antigen recognized by tumor-infiltrating lymphocytes associated with in vivo tumor rejection," *Proc. Natl. Acad. Sci. USA*, 91(14): 6458-6462 (Jul. 5, 1994).
Kawakami et al., "Recognition of Multiple Epitopes in the Human Melanoma Antigen gp100 by Tumor-Infiltrating T Lymphocytes Associated with In Vivo Tumor Regression," *The Journal of Immunology*, 154(8): 3961-3968 (Apr. 15, 1995).
Kawamoto et al., "Expression of the G2-M Checkpoint Regulators Cyclin B1 and cdc2 in Nonmalignant and Malignant Human Breast Lesions," *The American Journal of Pathology*, 150(1): 15-23 (Jan. 1997).
Keyomarsi et al., "Redundant cyclin overexpression and gene amplification in breast cancer cells," *Proc. Natl. Acad. Sci. USA*, 90(3): 1112-1116 (Feb. 1, 1993).
Kiessling et al., "Immunosuppression in Human Tumor-Host Interaction: Role of Cytokines and Alterations in Signal-Transducing Molecules," *Springer Seminars in Immunopathology*, 18(2): 227-242 (1996).
Kim et al., "Cyclin E Overexpression as an Independent Risk Factor of Visceral Relapse in Breast Cancer," *European Journal of Surgical Oncology*, 27: 464-471 (2001).
King et al., "Mitosis in Transition," *Cell*, 79: 563-571 (Nov. 18, 1994).
Klug et al., "Inactivation of a GFP Retrovirus Occurs at Multiple levels in Long Term Repopulating Stem Cells and Their Differentiated Progeny," *Blood*, 96(3): 894-901 (Aug. 1, 2000).
Koehne et al., "Phenotype of Lymphocyte Subsets After Autologous Peripheral Blood Stem Cell Transplantation," *Bone Marrow Transplant*, 19(2): 149-156 (Jan. 2, 1997).
Kondo et al., "Biology of Hematopoietic Stem Cells and Progenitors: Implications for Clinical Application," *Annul Review of Immunology*, 21: 759-806 (2003).
Kraulis et al., "MOLSCRIPT: A Program to Produce Both Detailed and Schematic Plots of Protein Structures," *Journal of Applied Crystallography*, 24(1): 946-950 (Feb. 1, 1991).

(56) References Cited

OTHER PUBLICATIONS

Kushner et al., "Aberrant Expression of Cyclin A and Cyclin B1 Proteins in Oral Carcinoma," *Journal of Oral Pathology & Medicine*, 28(2): 77-81 (Feb. 1999).
Lazar et al., "Transforming Growth Factor α: Mutation of Aspartic Acid 47 and Leucine 48 Results in Different Biological Activities," *Molecular and Cellular Biology*, 8(3): 1247-1252 (Mar. 1988).
Lennette et al., "Antibodies to LMP2A/2B in EBV-carrying Malignancies," *European Journal of Cancer*, 31A(11): 1875-1878 (1995).
Lin et al., "Structure-Function Relationships in Glucagon: Properties of Highly Purified Des-His$^1$-, Monoiodo-, and [Des-Asn$^{28}$, Thr$^{29}$](homoserine lactone$^{27}$)-glucagon," *Biochemistry*, 14(8): 1559-1563 (1975).
Luckow et al., "Trends in the Development of Baculovirus Expression Vectors," *Bio/Technology*, 6: 47-55 (Jan. 1988).
Lundstrom et al., "Latest development in viral vectors for gene therapy," *Trends in Biotechnology*, 21(3): 117-122 (Mar. 2003).
Magarian-Blander et al., "Specific and Effective T-Cell Recognition of Cells Transfected With a Truncated Human Mucin cDNA," *Ann N Y Acad Sci*, 690: 231-243 (1993).
Magarian-Blander et al., "Differential expression of MUC1 on transfected cell lines influences its recognition by MUC1 specific T cells," *Glycoconjugate Journal*, 13: 749-756 (1996).
Magarian-Blander et al., "Intercellular and Intracellular Events Following the MHC-Unrestricted TCR Recognition of a Tumor-Specific Peptide Epitope on the Epithelial Antigen MUC1," *Journal of Immunology*, 160(7): 3111-3120 (Apr. 1, 1998).
Martin et al., "Subfemtomole MS and MS/MS Peptide Sequence Analysis Using Nano-HPLC Micro-ESI Fourier Transform Ion Cyclotron Resonance Mass Spectrometry," *Analytical Chemistry*, 72(18): 4266-4274 (Sep. 15, 2000).
Mashal et al., "Expression of Cell Cycle-regulated Proteins in Prostate Cancer," *Cancer Research*, 56: 4159-4163 (Sep. 15, 1996).
Medzhitov et al., "Innate Immunity: The Virtues of a Nonclonal System of Recognition," *Cell*, 91(3): 295-298 (Oct. 31, 1997).
Merrifield, "Solid Phase Peptide Synthesis. I. The Synthesis of a Tetrapeptide," *J. Am. Chem. Soc.*, 85: 2149-2154 (Jul. 20, 1963).
Merritt et al., "Raster3D: Photorealistic Molecular Graphics." *Methods in Enzymology*, 277: 505-524 (1997).
Mittelbrunn et al., "Cutting Edge: Dynamic Redistribution of Tetraspanin CD81 at the Central Zone of the Immune Synapse in Both T Lymphocytes and APC," *Journal of Immunology*, 169(12): 6691-6695 (Dec. 15, 2002).
Molloy et al., "Production of Soluble Single-Chain T-Cell Receptor Fragments in *Escherichia coli* trxB Mutants," *Molecular Immunology*, 35(2): 73-81 (Feb. 1998).
Morgan et al., "High Efficiency TCR Gene Transfer into Primary Human Lymphocytes Affords Avid Recognition of Melanoma Tumor Antigen Glycoprotein 100 and Does Not Alter the Recognition of Autologous Melanoma Antigens," *Journal of Immunology*, 171(6): 3287-3295.(Sep. 15, 2003).
Murakami et al., "Determination of the prognostic significance of cyclin B1 overexpression in patients with esophageal squamous cell carcinoma," *Virchows Arch*, 434: 153-158 (1999).
Murray, "Cyclin Ubiquitination: The Destructive End of Mitosis," *Cell*, 81: 149-152 (Apr. 21, 1995).
Musgrove et al., "Cyclins and Breast Cancer," *Journal of Mammary Gland Biology and Neoplasia*, 1(2): 153-162 (1996).
NCBI "Chain B, Crystal Structure of Phospho-Cdk2 In Complex with Cyclin B," Database Entrez-Nucleotide, Accession No. 2JGZ_B (Jun. 20, 2007). Retrieved on Feb. 27, 2010.
NCBI "Cyclin B1 [*Homo sapiens*]," Database Entrez-Nucleotide, Accession No. AAV38930.1 (Oct. 28, 2004). Retrieved on Feb. 27, 2010.
NCBI "*Homo sapiens* cyclin B1 (CCNB1), mRNA," Database Entrez-Nucleotide, Accession No. NM_031966.2 (Jul. 2, 2011). Retrieved on Jul. 7, 2011.
NCBI "Mus musculus cyclin B1 (Ccnb1), mRNA," Database Entrez-Nucleotide, Acciession No. NM_172301.3 (May 15, 2011). Retrieved on Jul. 7, 2011.
NCBI "Unnamed Protein Product [*Homo sapiens*]," Database Entrez-Nucleotide, Accession No. BAF82120.1 (Oct. 28, 2004). Retrieved on Feb. 27, 2010.
Novotny et al., "A Soluble, Single-Chain T-Cell Receptor Fragment Endowed With Antigen-Combining Properties," *Proc Natl Acad Sci U S A*, 88(19): 8646-8650 (Oct. 1991).
Ohashi et al., "Efficient Transfer and Sustained High Expression of the Human Glucocerebrosidase Gene in Mice and Their Functional Macrophages Following Transplantation of Bone Marrow Transduced by a Retroviral Vector," *Proc Natl Acad Sci U S A*, 89: 11332-11336 (Dec. 1992).
Ostrand-Rosenberg, "Tumor Immunotherapy: The Tumor Cell as an Antigen-Presenting Cell," *Current Opinion of Immunology*, 6(5): 722-727 (1994).
Pavlinkova et al., "Pharmacokinetics and Biodistribution of a Light-Chain-Shuffled CC49 Single-Chain Fv antibody Construct," *Cancer Immunology Immunotherapy*, 49(4-5): 267-275 (2000).
Pearlman et al., "AMBER, A Package of Computer Programs for Applying Molecular Mechanics, Normal Mode Analysis, Molecular Dynamics and Free Energy Calculations to Simulate the Structural and Energetic Properties of Molecules," *Computer Physics Communications*, 91(1-3): 1-41 (Sep. 11, 1995).
Petit et al., "High level of single-nucleotide polymorphism in the rat cyclin B1 gene," *Mammalian Genome*, 10(6): 635-637 (1999).
Pinthus et al., "Immuno-Gene Therapy of Established Prostate Tumors Using Chimeric Receptor-redirected Human Lymphocytes," *Cancer Research*, 63(10): 2470-2476 (May 15, 2003).
Ressing et al., "Human CTL Epitopes Encoded by Human Papillomavirus Type 16 E6 and E7 Identified Through In Vivo and In Vitro Immunogenicity Studies of HLA-A*0201-Binding Peptides," *The Journal of Immunology*, 154(11): 5934-5943 (Jun. 1, 1995).
Restifo et al., "Identification of Human Cancers Deficient in Antigen Processing," *Journal of Experimental Medicine*, 177(2): 265-272 (Feb. 1, 1993).
Robbins et al., "A Mutated β-Catenin Gene Encodes a Melanoma-specific Antigen Recognized by Tumor Infiltrating Lymphocytes," *The Journal of Experimental Medical*, 183(3): 1185-1192 (Mar. 1, 1996).
Röpke et al., "Spontaneous human squamous cell carcinomas are killed by a human cytotoxic T lymphocyte clone recognizing a wild-type p53-derived peptide," *Proc. Natl. Acad. Sci. USA*, 93(25): 14704-14707 (Dec. 10, 1996).
Rosenberg et al., "Treatment of Patients With Metastatic Melanoma With Autologous Tumor-Infiltrating Lymphocytes and Interleukin 2," *Journal of the National Cancer Institute*, 86(15): 1159-1166 (Aug. 3, 1994).
Rosenfeld et al., "Adenovirus-Mediated Transfer of a Recombinant α1-Antitrypsin Gene to the Lung Epithelium in Vivo," *Science*, 252(5004): 431-434 (Apr. 19, 1991).
Rosenfeld et al., "In Vivo Transfer of the Human Cystic Fibrosis Gene to the Respiratory Epithelium," *Clinical Research*, 39(2): 311A (1991).
Rubinstein et al., "Transfer of TCR Genes into Mature T Cells Is Accompanied by the Maintenance of Parental T Cell Avidity," *Journal of Immunology*, 170(3): 1209-1217 (Feb. 1, 2003).
Sadovnikova et al., "Generation of Human Tumor-Reactive Cytotoxic T Cells Against Peptides Presented by Non-Self HLA Class I Molecules," *Eur. J. Immunol.*, 28: 193-200 (1998).
Saio et al., "Tumor-Infiltrating Macrophages Induce Apoptosis in Activated CD8$^+$ T Cells by a Mechanism Requiring Cell Contact and Mediated by Both the Cell-Associated Form of TNF and Nitric Oxide," *Journal of Immunology*, 167(10): 5583-5593 (Nov. 15, 2001).
Sanderson et al., "LacZ Inducible, Antigen/MHC-Specific T Cell Hybrids," *International Immunology*, 6(3): 369-376 (Mar. 1994).
Schafmeister et al., "LeAP," C.E.A.F., *University of California, San Francisco*, 1-191 (1995).
Schubert et al., "Rapid degradation of a large fraction of newly synthesized proteins by proteasomes," *Nature*, 404(6779): 770-774 (Apr. 13, 2000).
Schumacher, "T-Cell-Receptor Gene Therapy," *Nature*, 2: 512-519 (Jul. 2002).

(56) References Cited

OTHER PUBLICATIONS

Schwartz et al., "A superactive insulin: [B10-Aspartic acid]insulin(human)" *Proc. Natl. Acad. Sci.*, 84: 6408-6411 (Sep. 1987).
Shabanowitz et al., "Sequencing the Primordial Soup," *Mass Spectrometry in Biology and Medicine*, (Burlingame et al., eds.), 163-177 (Humana Press, Totowa, N.J., 2000).
Shively et al., "CEA-Related Antigens: Molecular Biology and Clinical Significance," *Critical Reviews in Oncology/Hematology*, 2(4): 355-399 (1985).
Skolnick et al., "From genes to protein structure and function: novel applications of computational approaches in the genomic era," *Trends in Biotech*,, 18: 34-39 (Jan. 2000).
Slamon et al., "Use of Chemotherapy Plus a Monoclonal Antibody Against HER2 for Metastatic Breast Cancer That Overexpresses HER2," *New England Journal of Medicne*, 344(11): 783-792 (Mar. 15, 2001).
Snyder et al., "Molecular Mechanisms and Biological Significance of CTL Avidity," *Current HIV Research*, 1(3): 287-294 (2003).
Soria et al., "Overexpression of Cyclin B1 in Early-Stage Non-Small Cell Lung Cancer and Its Clinical Implication," *Cancer Research*, 60(15): 4000-4004 (Aug. 1, 2000).
Stanislawski et al., "Circumventing Tolerance to a Human MDM2-Derived Tumor Antigen by TCR Gene Transfer," *Nature Immunology*, 2(10): 962-970 (Oct. 2001).
Steeg et al., "Cyclins and breast cancer," *Breast Cancer Research and Treatment*, 52: 17-28 (1998).
Tran et al., "Mitotic Cyclins and Cyclin-Dependent Kinases in Melanocytic Lesions," *Human Pathology*, 29(10): 1085-1090 (Oct. 1998).
Traversari et al. "A Nonapeptide Encoded by Human Gene MAGE-1 Is Recognized on HLA-A1 by Cytolytic T Lymphocytes Directed Against Tumor Antigen MZ2-E," *The Journal of Experimental Medicine*, 176: 1453-1457 (Nov. 1992).
Türeci et al., "Serological analysis of human tumor antigens: molecular definition and implications," *Molecular Medicine Today*, 3(8): 342-349 (Aug. 1997).
Van Den Eynde et al., "A New Family of Genes Coding for an Antigen Recognized by Autologous Cytolytic T Lymphocytes on a Human Melanoma," *The Journal of Experimental Medicine*, 182: 689-698 (Sep. 1995).
Van Der Bruggen et al., Autologous Cytolytic T Lymphocytes Recognize a MAGE-1 Nonapeptide on Melanomas Expressing HLA-Cw*1601*, *European Journal of Immunolgy*, 24(8): 2134-2140 (Sep. 1994).
Van Der Bruggen et al., "A Peptide Encoded by Human Gene MAGE-3 and Presented by HLA-A2 Induces Cytolytic T Lymphocytes That Recognize Tumor Cells Expressing MAGE-3*," *European Journal of Immunology*, 24(10): 3038-3043 (Dec. 1994).
Vlad et al., "Complex Carbohydrates Are Not Removed During Processing of Glycoproteins by Dendritic Cells: Processing of Tumor Antigen MUC1 Glycopeptides for Presentation to major Histocompatibility Complex Class II-Restricted T Cells," *Journal of Experimental Medicine*, 196(11): 1435-1446 (Dec. 2, 2002).
Wang et al., "Prostate Antigen: A New Potential Marker for Prostatic Cancer," *The Prostate*, 2(1): 89-96 (1981).
Wang et al., "Overexpression of cyclin B1 in human colorectal cancers," *Journal of Cancer Research and Clinical Oncology*, 123(2): 124-127 (1997).
Wang et al., "A T Cell-Independent Antitumor Response in Mice With Bone Marrow Cells Retrovirally Transduced With an Antibody/Fc-γ Chain Chimeric Receptor Gene Recognizing a Human Ovarian Cancer Antigen," *Nat Med*, 4(2): 168-172 (Feb. 1998).
Wang et al., "Cloning Genes Encoding MHC Class-II-Restricted Antigens: Mutated CDC27 as a Tumor Antigen," *Science*, 284: 1351-1354 (May 21, 1999).
Wang et al., "Human Tumor Antigens fo Cancer Vaccine Development," *Immunological Reviews*, 170: 85-100 (1999).
Weijtens et al., "Functional Balance Between T Cell Chimeric Receptor Density and Tumor Associated Antigen Density: CTL Mediated Cytolysis and Lymphokine Production," *Gene Therapy*, 7(1): 35-42 (Jan. 2000).
Willemsen et al., "Grafting Primary Human T Lymphocytes With Cancer-Specific Chimeric Single Chain and Two Chain TCR," *Gene Therapy*, 7(16): 1369-1377 (Aug. 2000).
Willemsen et al., "Genetic Engineering of T Cell Specificity for Immunotherapy of Cancer," *Human Immunology*, 64(1): 56-68 (2003).
Wölfel et al., "A $p16^{INK4a}$—Insensitive CDK4 Mutant Targeted by Cytolytic T Lymphocytes in a Human Melanoma," *Science*, 269(5228): 1281-1284 (Sep. 1, 1995).
Yang et al., "Antimelanoma Activity of CTL Generated from Peripheral Blood Mononuclear Cells After Stimulation with Autologous Dendritic Cells Pulsed with Melanoma gp100 Peptide G209-2M Is Correlated to TCR Avidity," *Journal of Immunology*, 169(1): 531-539 (Jul. 1, 2002).
Yasumura et al., "Human Cytotoxic T-Cell Lines with Restricted Specificity for Squamous Cell Carcinoma of the Head and Neck," *Cancer Research*, 53: 1461-1468 (Mar. 15, 1993).
Yee et al., "Adoptive T Cell Therapy Using Antigen-Specific $CD8^+$ T Cell Clones for the Treatment of Patients with Metastatic Melanoma: In Vivo Persistence, Migration, and Antitumor Effect of Transferred T Cells," *Proc Natl Acad Sci U S A*, 99(25): 16168-16173 (Dec. 10, 2002).
Yu et al., "Aberrant Cyclin B1 Expression in Human Tumors and Cell Lines," *FASEB Journal*, (Abstract 949.5) 15(5): A1206 (Mar. 2001).
Yu et al., "Immune Recognition of Cyclin B1 as a Tumor Antigen is a Result of its Overexpression in Human Tumors That is Caused by Non-Functional p53," *Molecular Immunology*, 38(12-13): 981-987 (May 2002).
Zeh III et al., "Flow-Cytometric Determination of Peptide-Class I Complex Formation Identification of p53 Peptides That Bind to HLA-A2," *Human Immunology*, 39(2): 79-86 (Feb. 1994).
Prosecution history of U.S. Appl. No. 10/253,867, filed Sep. 24, 2002, current as of Apr. 1, 2013.
Prosecution history of U.S. Appl. No. 11/295,767, filed Dec. 7, 2005, current as of Apr. 1, 2013.
Prosecution history of U.S. Appl. No. 11/366,196, filed Mar. 2, 2006, current as of Apr. 1, 2013.
Prosecution history of U.S. Appl. No. 12/258,545, filed Oct. 27, 2008, current as of Apr. 1, 2013.
Prosecution history of U.S. Appl. No. 12/698,822, filed Feb. 2, 2010, current as of Apr. 1, 2013.
European Patent Office, Supplementary Partial European Search Report dated Aug. 22, 2005, in 02797036.7.
European Patent Office, Supplementary Partial European Search Report dated Dec. 12, 2005, in 02797036.7.
European Patent Office, International Search Report dated Aug. 20, 2007, in PCT/US2005/044024.
Korean Intellectual Property Office, International Search Report dated Mar. 5, 2010, in PCT/US09/51853.
United States Patent and Trademark Office, International Search Report dated Oct. 8, 2003, in PCT/US02/30289.

\* cited by examiner

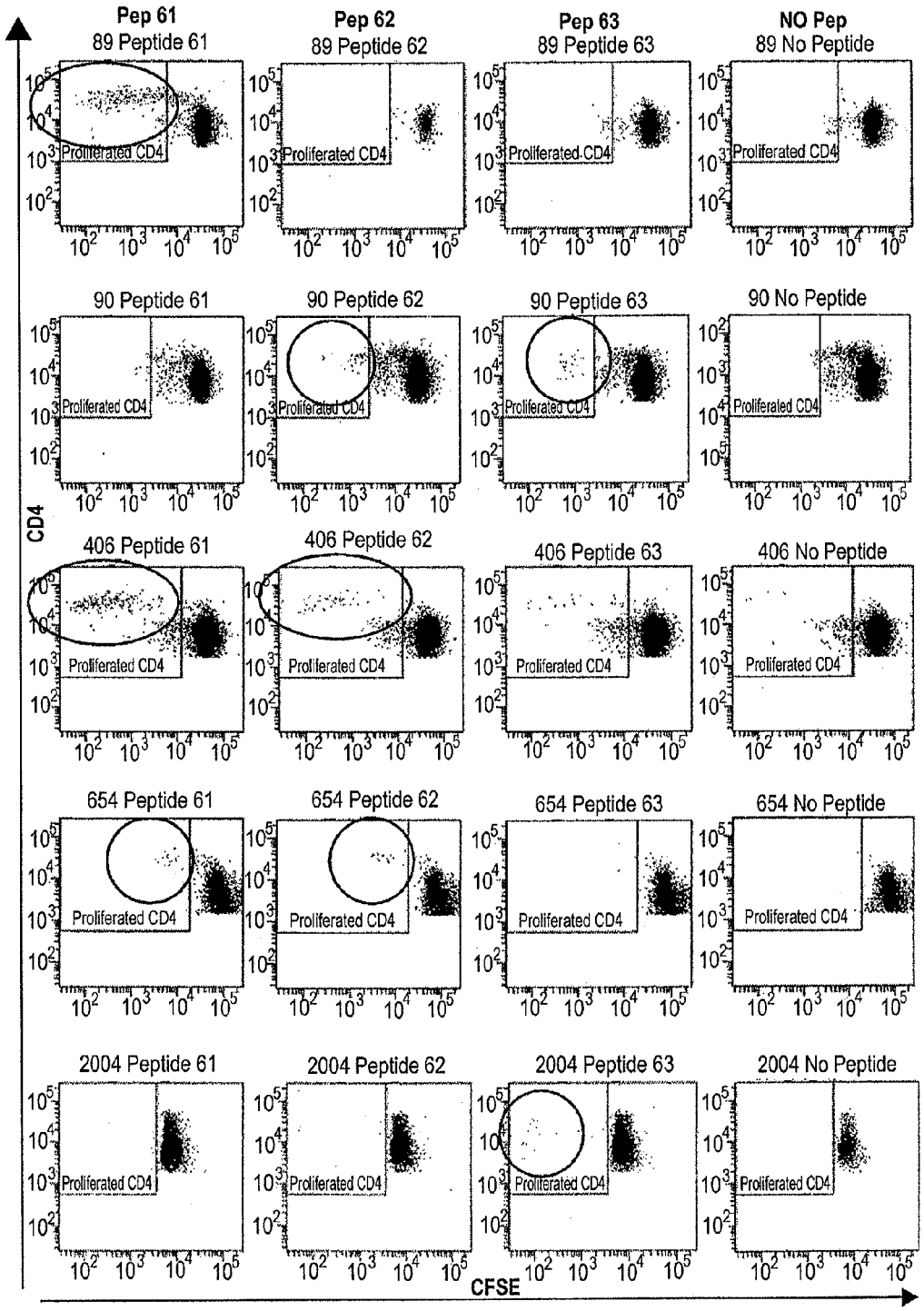

उस ८,७४८,१७० B२

POLYPEPTIDES DERIVED FROM CYCLIN B1 AND USES THEREOF

CROSS-REFERENCE TO RELATED APPLICATIONS

This patent application is the U.S. national phase of PCT/US2009/051853, filed on Jul. 27, 2009, which claims the benefit of U.S. Provisional Patent Application No. 61/083,800, filed Jul. 25, 2008, which is incorporated by reference.

STATEMENT REGARDING FEDERALLY SPONSORED RESEARCH AND DEVELOPMENT

This invention was made with Government support under grant number Pittsburgh Lung Cancer SPORE (NCI) 5P50 CA90440-07 and Immunology Predoctoral Training Grant #5T32CA82084-08, both awarded by the National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 4.00 KiloByte ASCII (Text) file named "707378 ST25.TXT," created on Dec. 23, 2010.

BACKGROUND OF THE INVENTION

U.S. patent application Ser. No. 11/366,196 (published as US 20060147460 A1), the entire contents of which are incorporated herein by reference, notes the desire for additional tumor antigens. While that application provides cyclin molecules and fragments derived from cyclin molecules as tumor antigens, additional tumor antigens are desired.

BRIEF SUMMARY OF THE INVENTION

In one embodiment, the invention provides a composition comprising one or more polypeptide(s), each of said polypeptide(s) comprising a sequence selected from the group consisting of KFRLLQETMYMTVSI (SEQ ID NO: 1), LQETMYMTVSIIDRF (SEQ ID NO: 2), and MYMTVSIIDRFM (SEQ ID NO: 3), or a combination of two or three such polypeptides, wherein each of said polypeptide(s) consist(s) of at most 24 amino acid residues, the composition also comprising a carrier.

In another embodiment, the invention provides a composition comprising one or more bacterial or viral vectors comprising one or more nucleic acid molecule(s) encoding one or more polypeptide(s), each of said polypeptide(s) having a sequence selected from the group consisting of KFRLLQETMYMTVSI (SEQ ID NO: 1), LQETMYMTVSIIDRF (SEQ ID NO: 2), and MYMTVSIIDRFM (SEQ ID NO: 3), wherein each of said polypeptide(s) consist(s) of at most 24 amino acid residues.

These and other aspects of the invention will become apparent upon reading the following detailed description in conjunction with the accompanying drawings.

BRIEF DESCRIPTION OF THE SEVERAL VIEWS OF THE DRAWING(S)

FIG. 1A and 1B: Cyclin B1 amino acids #215-233 contain an immunogenic region of cyclin B1 that stimulate T cell responses in the peripheral blood of heavy smokers who are negative for lung cancer by computed tomography (CT) scan. (FIG. 1A) CD4+T cells from 5 heavy smokers show proliferation in response to one or more of the inventive polypeptides: Pep61 (SEQ ID NO:1), Pep62 (SEQ ID NO:2); and Pep63 (SEQ ID NO:3). (FIG. 1B) Similarly, CD8+T cells from the same 5 individuals also are capable of proliferation in response to epitopes within amino acids 215-233. Cells considered to have proliferated above background (no peptide, on right) are circled.

FIG. 2A-2D: Cyclin B1 DNA prime-protein boost vaccination elicits cyclin B1-specific cellular and humoral responses and delays tumor growth. For (FIG. 2A) and (FIG. 2B), mice primed with either pcDNA 3.1 empty vector (group 1), mouse cyclin B1 (mCB1, group 2), or human cyclin B1 (hCB1, group 3) cDNA were boosted with human cyclin B1 recombinant protein and the LT/IS patch two times in 3 week intervals. (FIG. 2A) ELISPOT performed on mouse splenocytes. Error bars indicate standard deviation. (FIG. 2B) ELISA for anti-human (left) and anti-mouse (right) cyclin B1 IgG. Bars indicate geometric mean. For (FIG. 2C) and (FIG. 2D), mice from groups 1, 2, and 3 with the addition of untreated and pcDNA3.1 empty vector and LT/IS patch controls were challenged with LO2 tumor cells. (FIG. 2C) Tumor growth on day 28 after tumor challenge. Bars indicate mean tumor size. (FIG. 2D) Survival after tumor challenge (Logrank test, p<0.0001).

DETAILED DESCRIPTION OF THE INVENTION

In one embodiment, the invention provides a polypeptide having a sequence comprising, consisting of, or consisting essentially of from 10 to 24 (such as 10, 11, 12, 13, 14, 15, 16, 17, 18, 19, 20, 21, 22, 23, or 24) consecutive amino acids from residues 215-233 of the sequence of human cyclin B1 protein. The inventive polypeptide alternatively comprises, consists of, or consists essentially of from 10 to about 24 amino acids from the cyclin B1 protein from another animal, such as mouse, chimpanzee, or other homolog. The sequence of human cyclin B1 is known (GenBank Accession No. NM_031966), as is that of other animals (e.g., GenBank Accession No. NM_172301). Accordingly, ordinary skilled artisans are able to select suitable sequences of from about 10 to about 24 consecutive amino acids from residues 215-233 of the human cyclin B1 polypeptide or its homologs. Exemplary polypeptides of the present invention have sequences consisting of KFRLLQETMYMTVSI (SEQ ID NO:1), LQETMYMTVSIIDRF (SEQ ID NO:2), or MYMTVSIIDRFM (SEQ ID NO:3).

The inventive polypeptide can be produced by any suitable method. For example, it can be synthesized using standard direct peptide synthesizing techniques (Bodanszky, Principles of Peptide Synthesis (Springer-Verlag, Heidelberg: 1984)), such as via solid-phase synthesis (see, e.g., Merrifield, *J. Am. Chem. Soc.*, 85, 2149-54 (1963); Barany et al., *Int. J. Peptide Protein Res.*, 30, 705-739 (1987); and U.S. Pat. No. 5,424,398). Alternatively, a gene encoding the desired protein or peptide can be subcloned into an appropriate expression vector using well-known molecular genetic techniques. The protein or peptide can then be produced by a host cell and isolated from the cell. Any appropriate expression vector (see, e.g., Pouwels et al., Cloning Vectors: A Laboratory Manual (Elsevier, N.Y.: 1985)) and corresponding suitable host cells can be employed for production of the desired protein or peptide. Expression hosts include, but are not limited to, bacterial species, mammalian or insect host cell systems including baculovirus systems (see, e.g., Luckow et al., Bio/Technology, 6, 47 (1988)), and established cell lines such 293, COS-7, C127, 3T3, CHO, HeLa, BHK, etc.

Once it is manufactured and suitably isolated, the inventive polypeptide can be substantially purified by standard methods and formulated into a composition (e.g., including a pharmacologically- or physiologically-compatible carrier), lyophilized, or otherwise employed or preserved. Accordingly, the invention further comprises a composition comprising one or more of the inventive polypeptides and a carrier. For lyophilizing the composition, a carrier can include a lyoprotectant, such as sucrose. A pharmaceutically-acceptable composition can be formulated as a cream, wafer, dermal patch, spray, drop, suspension, emulsion, lozenge, tablet, capsule, or otherwise, as desired. Of course, in such compositions, suitable buffers, binders, glidants, preservatives, and other standard excipients can be included as desired, employing the ordinary skill of pharmaceutical compounding. For administration as a vaccine to patients, the composition typically will be formulated with carriers and buffers suitable for injection (e.g., parentarally or intratumorally). Many synthetic forms of the vaccine can be used, for example, a branched polymer can be synthesized to have a different peptide on each branch.

The invention also provides nucleic acid molecules encoding one or more of the inventive polypeptide sequences. The nucleic acid molecule can be administered to a patient as naked DNA or as a vector (e.g., bacterial or viral vectors) for use as a vaccine. Any suitable vector can be used. Examples of viral vectors include pox viruses, adenovirus, and HPV. Examples of bacterial vectors include recombinant salmonella and Listeria.

The polypeptide sequences can also be engineered into antibodies that target receptors on dendritic cells (example: anti-DEC-205 antibody) and these antibodies used as vaccines (see, e.g., Bozzacco et al., *Proc Nat. Acad. Sci. USA.* 2007 Jan. 23; 104(4):1289-94).

The inventive polypeptides are not restricted to a single HLA-Class I or HLA-Class II molecule as they elicit both CD8+ and CD4+ T cells in multiple individuals with multiple different HLA Class I and Class II types. Thus, the inventive cyclin B1 polypeptides can be mixed with HLA-A2 restricted cyclin B1 polypeptides (e.g., as described in U.S. patent application publication US 20060147460 A1) to provide help by stimulating CD4+ T cells as well as additional CD8+ T cells.

Using the inventive polypeptides, nucleic acid molecules, and antibodies, the invention provides a method for vaccinating a patient against cancer. In accordance with the method, a pharmaceutically-acceptable composition comprising one or more of the inventive polypeptides, nucleic acid molecules, and antibodies is administered to a patient in an amount and at a location sufficient to treat cancer in a patient having cancer or for prophylaxis of cancer in a patient at risk for developing the cancer. Typically, the patient will be a human who either has cancer or is determined to be at risk for developing cancer (e.g., having a genetic predisposition or family history of cancer). However, the patient alternatively can be a non-human animal, such as a common pets (cats, dogs, etc.), livestock (swine, cattle, sheep, goats, etc.), beasts of burden (horses, donkeys, elephants, camels, etc.), laboratory animals (mice, rats, and the like), or zoologically-important animals (e.g., endangered or threatened species or animals in captivity).

The inventive method can be used prophylactically or as a treatment for many types of cancer (e.g., cancers of bladder, bone, brain, breast, cervix, colon, epithelium, esophagus, head and neck, kidney, liver, lung, ovary, pancreas, prostate, skin, stomach, testicle, uterus, etc., and the various leukemias and lymphomas). Because Cyclin B1 appears to be overexpressed in cells that turn off the function of the tumor suppressor protein p53 (Yu et al., *Mol. Immunol.*, 38(12-13), 981-87 (2002)), tumors associated with disruption of p53 would be particularly attractive candidates for treatment in accordance with the present invention. Moreover, the polypeptides, nucleic acid molecules, and antibodies have the potential or capability to prevent or reduce the risk of developing cancer in individuals without cancer but who are or may become at risk of developing cancer. It will be observed that successful use of the inventive method does not require curing or complete remission of the cancer. It is sufficient if the method retards the progression of the cancer. Moreover, the inventive method can be used adjunctively with other methods of cancer treatment, such as through chemotherapy or radiotherapy.

The administration to a patient of a vaccine in accordance with this invention for prophylaxis and/or treatment of cancer can take place before or after a surgical procedure to remove the cancer, before or after a chemotherapeutic procedure for the treatment of cancer, or before or after radiation therapy for the treatment of cancer and any combination thereof. In addition, the vaccine can be given together with adjuvants and/or immuno-modulators to boost the activity of the vaccine and the patient's response. Moreover, additional inoculations of the vaccine (e.g., "booster" inoculations) can be employed as desired.

In one embodiment, a priming inoculation of the inventive nucleic acid molecule (e.g., formulated as a composition) can be administered to the patient, followed by one or more (e.g., one, two, three, four, or more) subsequent boosting inoculations of the inventive polypeptide (e.g., formulated as a composition), which is referred to as a DNA prime-protein boost vaccination protocol.

The boosting inoculation can be administered at any suitable time period after the priming inoculation (e.g., 1 week, 2 weeks, 3 weeks, 1 month, 2 months, 3 months, 4 months, 5 months, 6 months, 1 year, 2 years, 3 years, 4 years, 5 years, or 10 years). Similarly, if additional boosting inoculations are desired, the additional boosting inoculations (e.g., of the inventive polypeptide or nucleic acid molecules or compositions thereof) can be administered at any suitable time period after the initial boosting inoculation (e.g., 1 week, 2 weeks, 3 weeks, 1 month, 2 months, 3 months, 4 months, 5 months, 6 months, 1 year, 2 years, 3 years, 4 years, 5 years, or 10 years).

Following the inoculation(s), the patient's immune response to the antigen can be monitored, for example, by drawing blood from the patient and assessing the presence of immunoglobulins reactive against cyclin B1 or fragments thereof or for the presence of lymphocytes reactive against such polypeptides.

While, as mentioned, a pharmaceutically-acceptable composition according to the present invention can be formulated via standard methods as desired, typically the composition is formulated for injection for use in the inventive method. Desirably, the composition also can comprise an adjuvant. Preferred adjuvants are agonists of Toll-like receptors, and desirably a human Toll-like receptor (TLR). For use in human patients, preferably the composition includes one or more agonists of TLR1, TLR2, TLR3, TLR4, TLR5, TLR6, TLR7, TLR8, TLR9, or TLR10. However, the agonist can additionally target TLR11, TLR12, or TLR13. While any suitable TLR agonists can be employed, exemplary agonists suitable for use in the present invention include unmethylated CpG-containing polypeptides, Lipopolysacharide A (LPS), Monophosphoryl LipidA (MPL), and Poly-ICLC. Polypeptides also can be precipitated on Alum (aluminum salt), which is an FDA approved adjuvant for human vaccination.

Another composition suitable for use in the inventive method includes dendritic cells loaded with one or more of the inventive polypeptides or combination thereof. Methods for loading dendritic cells are known to persons or ordinary skill (see, e.g., U.S. patent application publication US 20060147460 A1 and Fay et al., *Cancer Immunol. Immunother.* 2006 October; 55(10):1209-18).

The following examples further illustrate the invention but, of course, should not be construed as in any way limiting its scope.

EXAMPLE 1

This example demonstrates the identification of three Cyclin B1 (CB1) polypeptides that carry immunogenic epitopes.

The amino acid sequence of the whole CB1 protein was synthesized as a series of peptides (generally 12-15 amino acids in length) that overlap by 11 amino acids (each peptide is offset by 4 amino acids). This approach is used when HLA of the subjects being tested is unknown and when there is a potential for multiple reactive peptides restricted by a variety of HLA molecules. It is also useful when the blood collection volumes are too small for dendritic cell generation, and other antigen presenting cells in the peripheral blood are counted on to present peptides without the need for further antigen processing.

Peripheral blood was collected into vaccutainers containing heparin sulfate and processed to obtain peripheral blood mononuclear cells (PBMC) by density centrifugation. PBMC were washed in PBS and labeled with 5 µM CFSE (Invitrogen) in warmed 0.1% FBS in PBS for 10 minutes at 37° C. The CFSE was quenched with 3 volumes of ice cold complete RPMI and incubated for 5 minutes before washes with complete RPMI. PBMC were then resuspended in media containing anti-CD28 and anti-CD49d antibodies for additional costimualtion. Wells coated with anti-CD3 were used as positive controls. Peptides were added at approximately 2 µg/ml. No peptide was added to negative control wells. After 6 days, cells were stained for cell surface markers and tested for proliferation by CFSE dilution using flow cytometry. Peptides that induced proliferation above that seen in the wells receiving no peptides were considered to be stimulatory.

The peptide library contained over 200 peptides divided into 10 pools. One of these pools repeatedly showed stimulation of T cells and when further analyzed, focused on 3 peptides that spanned amino acids #215-223 of the CB1 sequence. They are identified below according to their order in the peptide library as well as in the amino acid sequence:

```
                                          (SEQ ID NO: 1)
p61:    amino acids 215-229:    KFRLLQETMYMTVSI (SEQ ID NO: 2)
p62:    amino acids 219-233:    LQETMYMTVSIIDRF (SEQ ID NO: 3)
p63:    amino acids 223-234:    MYMTVSIIDRFM
```

Memory T cell responses specific for these peptides were observed in the blood samples obtained from heavy smokers who were enrolled in a lung cancer screening study and determined to be negative for lung cancer by CT. See FIGS. 1A and 1B.

EXAMPLE 2

This example demonstrates that CB1-specific immune responses can prevent tumor growth.

Given that healthy individuals have both humoral and cellular immune responses that are specific for the self and tumor antigen CB1, the potential significance of having anti-CB 1 immunity prior to the onset of cancer was explored. A transplantable mouse tumor model, a CB1 overexpressing lymphoma cell line (LO2) that was derived from a p53$^{-/-}$ mouse and spontaneously overexpresses CB1, was used. LO2 cells (maintained in vitro in RPMI-1640 medium (Gibco, Invitrogen) supplemented with 10% heat-inactivated fetal bovine serum (FBS, Cellgro; Media Tech Inc.), penicillin (100 U/ml), streptomycin (100 µg/ml), 0.3% glutamine (Gibco, Invitrogen), 0.1 mM non-essential amino acids, 1 mM sodium pyruvate, 10 µM (3-mercaptoethanol (Gibco, Invitrogen)) were subcutaneously inoculated into syngeneic C57Bl/6 mice to establish the transplantable tumor model.

Because overexpressed CB 1 in tumors is neither mutated nor altered postranslationally, it was expected that immune responses in healthy mice might be subject to self-tolerance and therefore difficult to elicit. For that reason, both mouse (self) and human (85% homologous but could be considered non-self) CB1 in two different forms, recombinant protein and cDNA, were chosen to test as immunogens. Transdermal delivery at the site of antigen injection of heat labile enterotoxin (LT) applied via an immunostimulatory (IS) patch was chosen as an adjuvant.

For the groups administered recombinant CB1 protein (i.e., the inventive polypeptide), C57Bl/6 mice were immunized subcutaneously with 25 µg/100 µl/mouse recombinant human cyclin B1 (hCB1) protein, mouse cyclin B1 protein (mCB1), or 100 µl PBS as a control. At the time of immunization or PBS treatment, an IS patch containing 20 µg heat-labile enterotoxin (LT) (IOMAI Corporation) was applied to the immunization site. Repeat injections and LT/IS patch application were repeated twice in 3 week intervals. Sera were collected to measure antibody response. Seventeen days after the last immunization, 3 mice per group were sacrificed to study T cell responses. The remaining mice from the hCB 1 and PBS groups, as well untreated, age-matched mice, were challenged with 1×10$^6$ LO2 cells subcutaneously. The protein plus adjuvant vaccine elicited CB1-specific CD4$^+$ T cells and IgG.

For the groups administered CB1 cDNA (i.e., a nucleic acid molecule encoding the inventive polypeptide), hCB 1 cDNA derived from a Hela cell line (from Dr. Qimin Zhan at the University of Pittsburgh) or mCB1 cDNA (an RT-PCR product derived from the mouse p53$^{-/-}$ LO2 cell line) was used. Briefly, RT-PCR was performed using forward primer ATGGCGCTCAGGGTCACTAG (SEQ ID NO:4) and reverse primer CAGTCTATTGGAGTTATGCCTTTG (SEQ ID NO:5). A band at approximately 1.3 kbp migrated on a 1.2% E-Gel Agarose gel (Invitrogen). The mCB1 band was eluted using a MiniElute Kit (Qiagen, Valencia, Calif.) and subcloned into PCR2.1-TOPO vector (Invitrogen) and used to transform One-Shot TOP10 competent cells (Invitrogen) as described by the manufacturer. Colonies were picked for culture, and plasmids were isolated and identified positively by an EcoRI digest. Both cDNAs were then subcloned into the BamHI-XhoI site of the pcDNA3.1 expression vector (Invitrogen). All inserts were verified by DNA sequencing.

Fifteen mice per group were immunized with either pcDNA3.1 control vector (group 1) or gene expression vectors encoding either mCB1 (group 2) or hCB1 (group 3) cDNA. Three weeks and 6 weeks later, mice were boosted with recombinant hCB 1 protein followed by the application of the LT/IS patch. Untreated mice and mice primed with empty pcDNA3.1 vector and boosted with LT/IS patch only were used as controls. Seventeen days after the last immunization, three mice per group were sacrificed for assessment of in vitro T cell responses and the remaining mice were challenged with LO2 tumor.

The DNA prime-protein boost vaccination induces CB1-specific T cell responses that can only partially be blocked by anti-CD4 antibody (groups 2 and 3). These results implied successful priming of CD8+ T cells, as well. The same results were obtained by boosting with mouse CB 1 protein, and in those experiments it was confirmed that CB 1 specific T cell responses can also be blocked by anti-CD8 antibody. CB1 DNA prime-protein boost vaccination also successfully elicited both anti-human and anti-mouse CB1 antibodies.

The presence of anti-CB 1 immune responses prior to tumor challenge significantly delayed or completely prevented tumor growth (see FIG. 2A-2D). By day 28 after tumor challenge, groups that received the DNA prime-protein boost vaccine had significantly lower mean tumor volume ($p<0.0001$) and significantly higher number of tumor-free mice ($p=0.0013$) than no treatment and adjuvant only controls. By day 42, all mice in the control groups were sacrificed due to excessive tumor burden, while 2 mice in group 1, 6 mice in group 2 and 5 mice in group 3 remained tumor free. Vaccination significantly enhanced survival. No evidence of self-tolerance to mCB1 was observed, since priming with mouse cDNA protected equally or slightly better than the hCB1 DNA vaccine. Similar protection was observed when the mCB1 DNA vaccine was boosted with mCB1 protein.

This data supports that the inventive polypeptides and nucleic acid molecules can be used to treat and prevent tumor growth.

All references, including publications, patent applications, and patents, cited herein are hereby incorporated by reference to the same extent as if each reference were individually and specifically indicated to be incorporated by reference and were set forth in its entirety herein. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. Preferred embodiments of this invention are described herein, including the best mode known to the inventors for carrying out the invention.

Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

The invention claimed is:

1. A composition comprising one or more polypeptide(s), each of said polypeptide(s) comprising a sequence selected from the group consisting of KFRLLQETMYMTVSI (SEQ ID NO: 1), LQETMYMTVSIIDRF (SEQ ID NO: 2), and MYMTVSIIDRFM (SEQ ID NO: 3), or a combination of two or three such polypeptides, wherein each of said polypeptide(s) consist(s) of at most 24 amino acid residues, the composition also comprising a carrier.

2. The composition of claim 1, wherein the carrier is a pharmaceutically-acceptable carrier.

3. The composition of claim 1, wherein said carrier is a lyoprotectant.

4. The composition of claim 1 in lyophilized form.

5. The composition of claim 1, which is a vaccine.

6. The composition of claim 1, further comprising an adjuvant.

7. The composition of claim 6, wherein the adjuvant comprises an agonist of a Toll-like receptor (TLR).

8. The composition of claim 7, wherein the TLR is a human TLR.

9. The composition of claim 7, wherein the TLR is TLR1, TLR2, TLR3, TLR4, TLR5, TLR6, TLR7, TLR8, TLR9, or TLR10.

10. The composition of claim 6, wherein the adjuvant is an unmethylated CpG-containing polypeptide, Lipopolysaccharide A (LPS), Monophosphoryl LipidA (MPL), Poly-ICLC, or a combination of two or more of these.

11. The composition of claim 6, wherein the adjuvant comprises Alum, onto which the polypeptide or combination of polypeptides has been precipitated.

12. The composition of claim 1, wherein the composition comprises dendritic cells loaded with said polypeptide or combination of polypeptides.

13. The composition of claim 1 formulated for injection.

14. The composition of claim 1, wherein at least one of said polypeptide(s) consists of the sequence consisting of KFRLLQETMYMTVSI (SEQ ID NO: 1).

15. The composition of claim 1, wherein at least one of said polypeptide(s) consists of the sequence consisting of LQETMYMTVSIIDRF (SEQ ID NO: 2).

16. The composition of claim 1, wherein at least one of said polypeptide(s) consists of the sequence consisting of MYMTVSIIDRFM (SEQ ID NO: 3).

17. The composition of claim 1, which comprises at least two polypeptides with distinct sequences.

18. The composition of claim 1, which comprises at least three polypeptides with distinct sequences.

19. The composition of claim 1, wherein each of said polypeptides consists of a sequence selected from the group consisting of KFRLLQETMYMTVSI (SEQ ID NO: 1), LQETMYMTVSIIDRF (SEQ ID NO: 2), and MYMTVSIIDRFM (SEQ ID NO: 3).

20. The composition of claim 19, which comprises at least two polypeptides with distinct sequences.

21. The composition of claim 19, which comprises at least three polypeptides with distinct sequences.

22. A composition comprising one or more bacterial or viral vectors comparing one or more nucleic acid molecule(s) encoding one or more polypeptide(s), each of said polypeptide(s) having a sequence selected from the group consisting of KFRLLQETMYMTVSI (SEQ ID NO: 1), LQETMYMTVSIIDRF (SEQ ID NO: 2), and MYMTVSIIDRFM (SEQ ID NO: 3), wherein each of said polypeptide(s) consist(s) of at most 24 amino acid residues.

23. The composition of claim 22, wherein at least one of said polypeptide(s) consists of the sequence consisting of KFRLLQETMYMTVSI (SEQ ID NO: 1).

24. The composition of claim 22, wherein at least one of said polypeptide(s) consists of the sequence consisting of LQETMYMTVSIIDRF (SEQ ID NO: 2).

25. The composition of claim 22, wherein at least one of said polypeptide(s) consists of the sequence consisting of MYMTVSIIDRFM (SEQ ID NO: 3).

26. The composition of claim 22, wherein one or more of said vectors is an expression vector.

* * * * *

UNITED STATES PATENT AND TRADEMARK OFFICE
CERTIFICATE OF CORRECTION

PATENT NO. : 8,748,170 B2
APPLICATION NO. : 13/055907
DATED : June 10, 2014
INVENTOR(S) : Finn et al.

Page 1 of 1

It is certified that error appears in the above-identified patent and that said Letters Patent is hereby corrected as shown below:

In the Specification

In Column 1, under the heading "STATEMENT REGARDING FEDERALLY SPONSORED RESEARCH AND DEVELOPMENT" the text beginning at Line 15 and ending at Line 19 is replaced as follows:
--This invention was made with Government support under Grant Numbers CA090440 and CA 082064 awarded by the National Institutes of Health. The Government has certain rights in the invention.--

Signed and Sealed this
First Day of January, 2019

Andrei Iancu
*Director of the United States Patent and Trademark Office*

SEQUENCE LISTING

```
<160> NUMBER OF SEQ ID NOS: 5

<210> SEQ ID NO 1
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 1

Lys Phe Arg Leu Leu Gln Glu Thr Met Tyr Met Thr Val Ser Ile
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 2

Leu Gln Glu Thr Met Tyr Met Thr Val Ser Ile Ile Asp Arg Phe
1               5                   10                  15

<210> SEQ ID NO 3
<211> LENGTH: 12
<212> TYPE: PRT
```

```
<213> ORGANISM: Artificial Sequence
<220> FEATURE:
<223> OTHER INFORMATION: Synthetic Sequence

<400> SEQUENCE: 3

Met Tyr Met Thr Val Ser Ile Ile Asp Arg Phe Met
1               5                   10

<210> SEQ ID NO 4
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 4
atggcgctca gggtcactag                                           20

<210> SEQ ID NO 5
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 5
cagtctattg gagttatgcc tttg                                      24
```